United States Patent
Hatsell et al.

(10) Patent No.: US 12,089,576 B2
(45) Date of Patent: *Sep. 17, 2024

(54) NUCLEIC ACIDS COMPRISING A MODIFIED RODENT ACTIVIN A RECEPTOR TYPE 1 (ACVR1) GENE

(71) Applicant: Regeneron Pharmaceuticals, Inc., Tarrytown, NY (US)

(72) Inventors: Sarah J. Hatsell, Nyack, NY (US); Aris N. Economides, Tarrytown, NY (US); Christopher Schoenherr, Piermont, NY (US); Vincent J. Idone, Ridgefield, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 20 days.

This patent is subject to a terminal disclaimer.

(21) Appl. No.: 17/811,089

(22) Filed: Jul. 7, 2022

(65) Prior Publication Data

US 2022/0369611 A1    Nov. 24, 2022

Related U.S. Application Data

(63) Continuation of application No. 16/439,068, filed on Jun. 12, 2019, now Pat. No. 11,419,319.

(60) Provisional application No. 62/828,532, filed on Apr. 3, 2019, provisional application No. 62/684,582, filed on Jun. 13, 2018.

(51) Int. Cl.
| | |
|---|---|
| *A01K 67/027* | (2024.01) |
| *A01K 67/0278* | (2024.01) |
| *C07H 21/02* | (2006.01) |
| *C07H 21/04* | (2006.01) |
| *C12N 15/00* | (2006.01) |

(52) U.S. Cl.
CPC ...... *A01K 67/0278* (2013.01); *A01K 2207/15* (2013.01); *A01K 2217/072* (2013.01); *A01K 2227/105* (2013.01); *A01K 2267/03* (2013.01)

(58) Field of Classification Search
USPC ...................................... 536/23.1; 435/320.1
See application file for complete search history.

(56) References Cited

U.S. PATENT DOCUMENTS

| | | | |
|---|---|---|---|
| 7,205,148 | B2 | 4/2007 | Economides et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 9,510,569 | B2 * | 12/2016 | Economides ...... A01K 67/0275 |
| 11,419,319 | B2 * | 8/2022 | Hatsell ............... A01K 67/0275 |
| 2006/0179501 | A1 | 8/2006 | Chan et al. |
| 2008/0078000 | A1 | 3/2008 | Poueymirou et al. |
| 2009/0253132 | A1 | 10/2009 | Kaplan et al. |
| 2011/0182904 | A1 | 7/2011 | Zimmerman et al. |
| 2014/0235933 | A1 | 8/2014 | Lee et al. |
| 2014/0283158 | A1 | 9/2014 | Economides et al. |
| 2014/0310828 | A1 | 10/2014 | Lee et al. |
| 2019/0380315 | A1 | 12/2019 | Hatsell et al. |

FOREIGN PATENT DOCUMENTS

| | | |
|---|---|---|
| CN | 104918484 A | 9/2015 |
| CN | 105142397 A | 12/2015 |
| CN | 107106648 A | 8/2017 |
| KR | 10-2016-0072795 A | 6/2016 |
| RU | 2 425 880 C2 | 2/2011 |
| WO | 02/088353 A2 | 11/2002 |
| WO | 02/088353 A3 | 11/2002 |
| WO | 2007/123896 A2 | 11/2007 |
| WO | 2011/059799 A1 | 5/2011 |
| WO | 2014/160429 A1 | 10/2014 |

OTHER PUBLICATIONS

Ageta-Ishihara N. et al., "Chronic Overload of SEPT4, a Parkin Substrate that Aggregates in Parksinson's Disease, Causes Behavioral Alternations But Not Neurodegeneration in Mice", Molecular Brain 6(35):1-14 (2013).
Chakkalakal S A et al., "Palovarotene Inhibits Heterotopic Ossification and Maintain Limb Mobility and Growth in Mice With the Human ACVR1R206H Fibrodysplasia Ossificans Progressiva (FOP) Mutation", Journal of Bone and Mineral Research 31(9):1666-1675 (Sep. 2016).
Chakkalakal S A et al., "An Acvr1 R206H Knock-In Mouse Has Fibrodysplasia Ossificans Progressiva", Journal of Bone and Mineral Research 27(8):1746-1756 (Aug. 2012).
Cowan PJ et al., "Targeting Gene Expression to Endothelium in Transgenic Animals: A Comparison of the Human CAM-2, PECAM-1 and Endoglin Promoters", Xenotransplantation 10:223-231 (2003).
Feil R. et al., "Regulation of Cre Recombinase Activity by Mutated Estrogen Receptor Ligand-Binding Domains", Biochemical and Biophysical Research Communications 237(3):752-757 (1997).
Fukuda T. et al., "Generation of a Mouse With Conditionally Activated Signaling Through the BMP Receptor, ALK2", Genesis 44:159-167 (2006).
Glaser D.L. et al., "In Vivo Somatic Cell Gene Transfer of an Engineered Noggin Mutein Prevents BMP4-Induced Heterotopic Ossification", The Journal of Bone and Joint Surgery 85-A(12):2332-2342 (Dec. 2003).
Gómez-Rodríguez J. et al., "Advantages of q-PCR as a Method of Screening for Gene Targeting in Mammalian Cells Using Conventional and Whole BAC-Based Constructs", Nucleic Acids Research 36(18):e117 (2008).

(Continued)

*Primary Examiner* — Michael C Wilson
(74) *Attorney, Agent, or Firm* — Scully, Scott, Murphy & Presser, P.C.; Shing-Yi Cheng

(57) ABSTRACT

A genetically modified rodent is provided that comprises a modified Acvr1 gene that comprises a conditional altered exon 7 encoding R258G in antisense orientation, flanked by site-specific recombinase recognition sites, wherein the altered exon is inverted to sense orientation upon action of a recombinase, resulting in ectopic bone formation.

12 Claims, 3 Drawing Sheets
Specification includes a Sequence Listing.

(56) References Cited

OTHER PUBLICATIONS

Harari D. et al., "Bridging the Species Divide: Transgenic Mice Humanized for Type-1 Interferon Response", PLoS One 9(1):e84259 (Jan. 2014).
Hatsell S.J. et al., "ACVR1R206H Receptor Mutation Causes Fibrodysplasia Ossificans Progressiva by Imparting Responsiveness to Activin A", Science Translational Medicine 7(303):303ra137 (Sep. 2, 2015).
Holkers M. et al., "Nonspaced Inverted DNA Repeats are Preferential Targets for Homology-Directed Gene Repair in Mammalian Cells", Nucleic Acids Research 40(5):1984-1999 (2012).
Indra A K et al., "Temporally-Controlled Site-Specific Mutagenesis in the Basal Layer of the Epidermis: Comparison of the Recombinase Activity of the Tamoxifen-Inducible Cre-ERT and Cre-ERT2 Recombinases", Nucleic Acids Research 27(22):4324-4397 (1999).
Kan L. et al., "Animal Models of Typical Heterotopic Ossification", Journal of Biomedicine and Biotechnology 2011: IDS309287, 8 pages (2011).
Kan L. et al., "Transgenic Mouse Overexpressing BMP4 Develop a Fibrodysplasia Ossificans Progressive (FOP)-Like Phenotype", American Journal of Pathology 165(4):1107-1115 (Oct. 2004).
Kaplan F.S. et al., "Multi-System Involvement in a Severe Variant of Fibrodysplasia Ossificans Progressiva (ACVR1 c.772G>A; R258G): A Report of Two Patients", American Journal of Medical Genetics Part A 167A:2265-2271 (2015).
Mishina Y. et al., "Multiple Roles for Activin-Like Kinase-2 Signaling During Mouse Embryogenesis", Developmental Biology 231:314-326 (1999).
Pignolo R J et al., "Fibrodysplasia Ossificans Progressiva: Clinical and Genetic Aspects", Orphanet Journal of Rare Diseases 6(80):1-6 (2011).
Schnütgen F. et al., "A Directional Strategy for Monitoring Cre-Mediated Recombinant at the Cellular Level in the Mouse", Nature Biotechnology 21: 562-565 (May 2003).

Shore E M et al., "A Recurrent Mutation in the BMP Type I Receptor ACVR1 Causes Inherited and Sporadic Fibrodysplasia Ossificans Progressiva", Nature Genetics 36(5):525-527 (2006).
Stoeger T et al., "In Situ Gene Expression Analysis During BMP2-Induced Ectopic Bone Formation in Mice Shows Simultaneous Endochondral and Intramembranous Ossification", Growth Factors 20(4):197-210 (2002).
Valenzuela D. et al., "High-Throughput Engineering of the Mouse Genome Coupled With High-Resolution Expression Analysis", Nature Biotechnology 21(6):652-659 (Jun. 2003).
Wolken D.M.A. et al., "The Obligatory Role of Activin A in the Formation of Heterotopic Bone in Fibrodysplasia Ossificans Progressiva", Bone 109:210-217 (2018).
Yu P B et al., "BMP Type I Receptor Inhibition Reduces Heterotopic Ossification", Nature Medicine 14(12):1363-1369 (Dec. 2008).
International Search Report and Written Opinion dated Oct. 10, 2019 received in International Application No. PCT/US2019/036719.
International Preliminary Report on Patentability and Written Opinion dated Sep. 24, 2015 received in International Application No. PCT/US2014/026582.
International Search Report and Written Opinion dated Aug. 4, 2014 received in International Application No. PCT/US2014/026582.
Dennis, Jr. M.B., "Welfare Issues of Genetically Modified Animals", ILAR Journal 43(2):100-109 (2002).
Glick B. et al., Moleculyarnaya Biotehnologiya. Printsipy i primeneniye. Moscow: Mir, 2002, together with an English-language translation.
Zhou H. et al., "Developing ITA Transgenic Rats for Inducible and Reversible Gene Expression", International Journal of Biological Sciences 5(2):171-181 (2009).
Russian Office Action & Search Report dated Oct. 6, 2022 received in Russian Application No. 2020135438/10 (065326), together with an English-language translation.
Kaplan F.S et al., Granting Immunity to FOP and Catching Heterotopic Ossification in the Act, Seminars in Cell and Developmental Biology 49:30-36 (Jan. 2016).
Chinese Search Report dated Jun. 27, 2024 received in Chinese Application No. 2019800390592, together with an English-language translation.

* cited by examiner

NUCLEIC ACIDS COMPRISING A MODIFIED RODENT ACTIVIN A RECEPTOR TYPE 1 (ACVR1) GENE

CROSS REFERENCE TO RELATED APPLICATIONS

This application is a continuation of U.S. patent application Ser. No. 16/439,068, filed Jun. 12, 2019, which claims the benefits of priority from U.S. Provisional Application No. 62/828,532, filed Apr. 3, 2019, and U.S. Provisional Application No. 62/684,582, filed Jun. 13, 2018, the entire contents of which are incorporated herein by reference.

FIELD OF THE DISCLOSURE

This disclosure relates to genetically modified rodent animals and rodent models of human diseases. More specifically, this disclosure relates to genetically modified rodents whose genome comprises a modified rodent Acvr1 gene; rodents that exhibit a phenotypical feature of fibrodysplasia ossificans progressiva (FOP) such as ectopic bone formation; isolated rodent tissues and cells whose genome comprises a modified rodent Acvr1 gene; isolated nucleic acids that comprise a modified rodent Acvr1 gene; compositions and methods of making the genetically modified rodents; methods of breeding; and methods of using the genetically modified rodents.

INCORPORATION BY REFERENCE OF SEQUENCE LISTING

The sequence listing in the XML, named as 36190Z_10461 US02_SequenceListing.xml of 10 KB, created on Jul. 6, 2022, and submitted to the United States Patent and Trademark Office via Patent Center, is incorporated herein by reference.

BACKGROUND ART

Various publications, including patents, patent applications, published patent applications, accession numbers, technical articles and scholarly articles are cited throughout the specification. Each of these cited publications is incorporated by reference, in its entirety and for all purposes, in this document.

Acrv1 is a type I receptor for bone morphogenic proteins (BMPs). Certain mutations in the human ACVR1 gene, including mutations that give rise to the amino acid modification R206H or R258G, are strongly associated with the disease fibrodysplasia ossificans progressiva (FOP) (see, e.g., US Pat. Appl. Publ. No. 2009/0253132; Pignolo, R. J. (2011) Orphanet Journal of Rare Diseases, 6:80, 1-6; and Kaplan et al., Am J Med Genet A. 2015; 167(10): 2265-2271). Chimeric mice that bear an R206H mutation in Acvr1 develop an FOP-like phenotype (see, e.g., Chakkalakal et al. (2012) J. Bone and Mineral Res. 27:1746-1756). Certain mutations in the Acvr1 gene, e.g., those resulting in an R206H Acvr1 protein variant, are perinatal lethal in mice and present challenges for passing a knock-in gene comprising the mutation through the germline of a rodent.

SUMMARY OF THE DISCLOSURE

This disclosure is directed to genetically modified rodent animals that comprise in their germline a nucleic acid sequence that comprises a modified rodent Acvr1 gene.

Genetically modified rodent animals are provided that comprise in their germline a nucleic acid sequence that comprises a modified rodent Acvr1 gene, wherein the modified rodent Acvr1 gene comprises a conditional alteration of a rodent Acvr1 gene, wherein the alteration renders the rodent animal susceptible to ectopic bone formation.

Genetically modified rodent animals are provided that comprise in their germline a nucleic acid sequence that comprises a modified rodent Acvr1 gene comprising a conditional altered Acvr1 exon, wherein induction of expression of the conditional altered Acvr1 exon confers upon the rodent animal a susceptibility to ectopic bone formation. In one embodiment, the altered Acvr1 exon is exon 7. In a specific embodiment, the altered Acvr1 exon 7 includes an alteration resulting in a R258G amino acid variation in Acvr1 protein.

Rodent animals are provided that conditionally express an altered Acvr1 allele. In various aspects, the altered Acvr1 allele is an allele that confers a pathological phenotype on the rodent animal expressing the allele. In various aspects, the rodent animals comprise an altered exon of an Acvr1 allele flanked upstream and downstream with site-specific recombinase recognition sites (SRRS's), and the rodent animal comprises a recombinase that recognizes the SRRS's, wherein the activity of the recombinase is inducible.

Rodent animals are provided that comprise a modification of a rodent Acvr1 gene that causes (in one embodiment, in a heterozygote; in one embodiment, in a homozygote), promotes, or makes the rodent animal susceptible to ectopic bone formation Rodent animals are provided that comprise a conditional alteration of a rodent Acvr1 gene, wherein an altered Acvr1 allele is not expressed in utero, and is not expressed perinatally, and wherein the rodent animals express the altered Acvr1 allele in a conditional manner, wherein the conditional expression is induced by administration of a compound of interest to the rodent animal.

In one aspect, a rodent animal is provided whose genome comprises a modified rodent Acvr1 locus comprising an altered Acvr1 exon in antisense orientation, wherein the altered Acvr1 exon is flanked upstream and downstream by SRRS's that are oriented to direct an inversion when acted upon by a recombinase that recognizes the SRRS's.

In some embodiments, a rodent animal is provided whose genome comprises a modified rodent Acvr1 gene within an endogenous rodent Acvr1 locus, the modified rodent Acvr1 gene comprising a functioning Acvr1 exon 7 in sense orientation and flanked upstream and downstream by a first pair of SRRS', and an altered Acvr1 exon 7 in antisense orientation and flanked upstream and downstream by a second pair of SRRS', wherein the first and second pairs of SRRS' are orientated such that a recombinase can invert the altered Acvr1 exon 7 into sense orientation and delete the functioning Acvr1 exon 7, resulting in an altered Acvr1 allele (i.e., an Acvr1 allele comprising the alteration). In various embodiments, except for exon 7, the remaining exons of a modified rodent Acvr1 gene are functioning exons of an endogenous rodent Acvr1 gene, e.g., wild type rodent exons present at an endogenous rodent Acvr1 locus. In various embodiments, the altered Acvr1 allele is an allele that confers a pathological phenotype on the rodent animal expressing the allele.

In some embodiments, provided herein is a genetically modified rodent whose genome comprises a modified rodent Acvr1 gene within an endogenous rodent Acvr1 locus, wherein the modified rodent Acvr1 gene comprises (a) a functioning Acvr1 exon 7 encoding R258 in sense orientation, flanked upstream and downstream by a first pair of SRRS'; and (b) an altered rodent Acvr1 exon 7 encoding a R258G variation in antisense orientation, flanked by a second pair of SRRS' that are different from the first pair of SRRS'; wherein the first and second pairs of SRRS' are oriented so that a recombinase can invert the altered rodent Acvr1 exon 7 into sense orientation, delete the functioning Acvr1 exon 7, and allow an altered Acvr1 allele comprising the altered rodent Acvr1 exon 7 to be expressed. In some embodiments, expression of an altered Acvr1 allele comprising the altered rodent Acvr1 exon 7 results in ectopic bone formation. In various embodiments, except for exon 7, the remaining exons of a modified rodent Acvr1 gene are functioning exons of an endogenous rodent Acvr1 gene, e.g., wild type rodent exons present at an endogenous rodent Acvr1 locus.

In some embodiments, a functioning Acvr1 exon 7 encoding R258 is a naturally occurring, functioning rodent Acvr1 exon 7, i.e., a wild type rodent Acvr1 exon 7. In some embodiments, a functioning Acvr1 exon 7 encoding R258 is a substantially human ACVR1 exon 7. In some embodiments, a substantially human ACVR1 exon 7 is a naturally occurring, functioning human ACVR1 exon 7, i.e., a wild type human ACVR1 exon 7. In other embodiments, a substantially human ACVR1 exon 7 differs from a wild type human ACVR1 exon 7 by at least one nucleotide (i.e., one or more nucleotides) and has a reduced sequence identity with an altered rodent Acvr1 exon 7 as compared to the sequence identity between the wild type human ACVR1 exon 7 and the altered rodent Acvr1 exon 7. In some embodiments, a substantially human ACVR1 exon 7 encodes the same amino acids as a wild type human ACVR1 exon 7.

In some embodiments, the first pair of SRRS' includes a first SRRS and a second SRRS, wherein the first and second SRRS' are compatible with each other and are oriented to direct an inversion. In some embodiments, the second pair of SRRS' includes a third SRRS and a fourth SRRS, wherein the third and fourth SRRS' are compatible with each other, are oriented to direct an inversion, but are not compatible with the first or second SRRS.

In some embodiments, a genetically modified rodent is provided that comprises a modified rodent Acvr1 gene at an Acvr1 locus in the germline of the rodent, wherein the modified rodent Acvr1 gene comprises, with respect to the direction of transcription of the Acvr1 gene, (i) a functioning exon 7 (e.g., a substantially human exon 7) in sense orientation, and (ii) an altered exon 7 in antisense orientation; and comprises a first pair of SRRS' composed of a first SRRS (SRRS1) and a second SRRS (SRRS2), and a second pair of SRRS' composed of a third SRRS (SRRS3) and a fourth SRRS (SRRS4); wherein SRRS1 is compatible with SRRS2, SRRS3 is compatible with SRRS4, but neither SRRS1 nor SRRS2 is compatible with SRRS3 or SRRS4, wherein SRRS1 is located upstream of the functioning exon 7, SRRS2 is located just downstream (with respect to transcriptional direction of the Acvr1 gene) of the antisense altered exon 7, wherein SRRS1 and SRRS2 are oriented to direct an inversion; wherein SRRS3 is disposed between the functioning exon 7 and the altered antisense exon 7, and SRRS4 is located downstream (with respect to the direction of orientation of the Acvr1 gene) of SRRS2, wherein SRRS3 and SRRS4 are oriented to direct an inversion. In some embodiments, each of SRRS' 1-4 is recognized by the same recombinase, such as Cre.

In some embodiments, the first pair of SRRS' is a pair of Lox2372 sites, and the second pair of SRRS' is a pair of LoxP sites. In other embodiments, the first pair of SRRS' is a pair of LoxP sites, and the second pair of SRRS' is a pair of Lox2372 sites.

In some embodiments, a genetically modified rodent animal further comprises an inducible recombinase which recognizes the SRRS's and is capable of inverting the antisense altered Acvr1 exon to sense orientation. In one embodiment, the gene encoding the inducible recombinase is in the germline of the rodent, e.g., integrated at an endogenous rodent ROSA26 locus.

Inducibility of a recombinase can be achieved at the transcription (gene expression) level, or at the protein activity level. In some embodiments, expression of the recombinase gene is inducible, and/or developmentally regulated, and/or specific to certain tissue or cell types. In other embodiments, expression of the recombinase gene is constitutive, and the activity of the recombinase is inducible.

In some embodiments, the recombinase is Cre. In some embodiments, the SRRS's are lox sites or variants thereof which are recognized by Cre. In some embodiments, a recombinase (e.g., Cre) is fused to a ligand binding domain responsive to binding by a ligand. In some embodiments, a recombinase (e.g., Cre) is fused to a ligand binding domain that is the ligand binding domain of a receptor such as a steroid receptor, a glucocorticoid receptor, a retinoid receptor, a thyroid receptor, or an estrogen receptor (ER), or that is derived from the ligand binding domain of a receptor. In some embodiments, Cre is fused to an ER ligand-binding domain comprising T2 mutations (referred to herein as Cre-ER$^{T2}$). A Cre-ER$^{T2}$ fusion protein is responsive to (i.e., activated by) binding by a ligand, e.g., tamoxifen or a functional analogs/derivative thereof. In one embodiment, a gene encoding CreER$^{T2}$ is present at the ROSA26 locus of a genetically modified rodent.

In some embodiments, a mutant rodent is provided that is derived from a genetically modified rodent described above (i.e., derived from a genetically modified rodent comprising a modified rodent Acvr1 gene which comprises a conditional Acvr1 alteration in antisense orientation), wherein the mutant rodent has a genome that comprises the Acvr1 alteration in sense orientation and wherein an Acvr1 gene comprising the alteration is expressed in the mutant rodent which, in some embodiments, results in ectopic bone formation.

In one embodiment, the genetically modified rodent is a mouse having the genotype Acvr1$^{[R258G]FlEx/+}$; Gt(ROSA26)Sor$^{CreERt2/+}$.

In some embodiments, a genetically modified rodent is provided that expresses an Acvr1 allele comprising a functioning Acvr1 exon 7 (e.g., in utero and perinatally), wherein upon action of the genetically modified rodent by a recombinase, the rodent expresses a variant Acvr1 protein comprising a R258G amino acid variation.

In some embodiments, an adult rodent is provided that expresses an Acvr1 gene product characterized by a R258G variation, wherein at least 40%, 50%, 60%, 70%, 80%, 90%, 95%, or 99% of the cells of the rodent comprise an altered Acvr1 gene encoding the R258G variation. In other embodiments, an adult rodent is provided that expresses an Acvr1 gene product characterized by a R258G variation in specific tissues or cell types.

In some embodiments, a genetically modified rodent is provided, wherein the rodent comprises a modified rodent Acvr1 locus in its germline that, upon action by a recombinase, expresses an Acvr1 protein that comprises a R258G variation.

In some embodiments, a rodent is provided that expresses a protein variant comprising a R258G variation, wherein the rodent is non-chimeric (i.e., all the cells in the rodent express the variant protein). In some embodiments, a rodent is provided that expresses a protein variant comprising a R258G variation, wherein at least 40%, 50%, 60%, 70%, 80%, 90%, 95%, or 99% of the cells of the rodent express the protein variant.

In some embodiments, a rodent is provided that expresses a protein variant from a modified rodent Acvr1 locus in the germline of the rodent, wherein all Acvr1-expressing cells of the rodent comprise a modified rodent Acvr1 gene that encodes an Acvr1 protein that comprises an R258G variation. In one embodiment, all germ cells of the rodent comprise a modified rodent Acrv1 locus comprising a conditional genetic modification that encodes an Acvr1 protein with an R258G variation.

In some embodiments, a genetically modified rodent is heterozygous for the genetic modification, i.e., the modified rodent Acvr1 gene comprising a conditional alteration. In some embodiments, the rodent is homozygous for the genetic modification.

In various embodiments, a genetically modified rodent is selected from the group consisting of a mouse, a rat, and a hamster. In some specific embodiments, the rodent is a mouse. In some specific embodiments, the rodent is a rat.

In another aspect, disclosed herein is a nucleic acid comprising a modified rodent Acvr1 gene described herein.

In some embodiments, a modified rodent Acvr1 gene in a nucleic acid comprises a functioning Acvr1 exon 7 in sense orientation, flanked upstream and downstream by a first pair of SRRS', and an altered Acvr1 exon 7 in antisense orientation, flanked upstream and downstream by a second pair of SRRS', wherein the first and second pairs of SRRS' are orientated such that a recombinase can invert the altered Acvr1 exon 7 into sense orientation, and delete the functioning Acvr1 exon 7. In various embodiments, except for exon 7, the remaining exons of a modified rodent Acvr1 gene are functioning exons of a rodent Acvr1 gene, e.g., wild type exons of an endogenous rodent Acvr1 gene.

In some embodiments, a modified rodent Acvr1 gene in a nucleic acid comprises (a) a functioning Acvr1 exon 7 encoding R258 in sense orientation, flanked upstream and downstream by a first pair of SRRS'; and (b) an altered rodent Acvr1 exon 7 encoding a R258G variation in antisense orientation, flanked by a second pair of SRRS' that are different from the first pair of SRRS'; wherein the first and second pairs of SRRS' are oriented so that a recombinase can invert the altered rodent Acvr1 exon 7 into sense orientation, delete the functioning Acvr1 exon 7, and allow an altered Acvr1 allele comprising the altered rodent Acvr1 exon 7 to be expressed. In some embodiments, expression of an altered Acvr1 allele comprising the altered rodent Acvr1 exon 7 results in ectopic bone formation. In various embodiments, except for exon 7, the remaining exons of a modified rodent Acvr1 gene are functioning exons of a rodent Acvr1 gene, e.g., wild type exons of a rodent Acvr1 gene.

In some embodiments, a functioning Acvr1 exon 7 encoding R258 is a wild type rodent Acvr1 exon 7. In some embodiments, a functioning Acvr1 exon 7 encoding R258 is a substantially human ACVR1 exon 7. In some embodiments, a substantially human ACVR1 exon 7 is a wild type human ACVR1 exon 7. In other embodiments, a substantially human ACVR1 exon 7 differs from a wild type human ACVR1 exon 7 by at least one nucleotide and has a reduced sequence identity with an altered rodent Acvr1 exon 7 as compared to the sequence identity between the wild type human ACVR1 exon 7 and the altered rodent Acvr1 exon 7. In some embodiments, a substantially human ACVR1 exon 7 encodes the same amino acids as a wild type human ACVR1 exon 7.

In some embodiments, the first pair of SRRS' includes a first SRRS and a second SRRS, wherein the first and second SRRS' are compatible with each other and are oriented to direct an inversion. In some embodiments, the second pair of SRRS' includes a third SRRS and a fourth SRRS, wherein the third and fourth SRRS' are compatible with each other, are oriented to direct an inversion, but are not compatible with the first or second SRRS.

In some embodiments, a modified rodent Acvr1 gene in a nucleic acid comprises, with respect to the direction of transcription of the Acvr1 gene, (i) a functioning exon 7 (e.g., a substantially human exon 7) in sense orientation, and (ii) an altered exon 7 in antisense orientation; and comprises a first pair of SRRS' composed of a first SRRS (SRRS1) and a second SRRS (SRRS2), and a second pair of SRRS' composed of a third SRRS (SRRS3) and a fourth SRRS (SRRS4); wherein SRRS1 is compatible with SRRS2, SRRS3 is compatible with SRRS4, but neither SRRS1 nor SRRS2 is compatible with SRRS3 or SRRS4, wherein SRRS1 is located upstream of the functioning exon 7, SRRS2 is located just downstream (with respect to transcriptional direction of the Acvr1 gene) of the antisense altered exon 7, wherein SRRS1 and SRRS2 are oriented to direct an inversion; wherein SRRS3 is disposed between the functioning exon 7 and the altered antisense exon 7, and SRRS4 is located downstream (with respect to the direction of orientation of the Acvr1 gene) of SRRS2, wherein SRRS3 and SRRS4 are oriented to direct an inversion. In some embodiments, each of SRRS' 1-4 is recognized by the same recombinase, such as Cre.

In another aspect, disclosed herein is a rodent genome comprising a nucleic acid that comprises a modified rodent Acvr1 gene, described above.

In some embodiments, the rodent genome further comprises a gene encoding an inducible recombinase that recognizes the SRRS' and is capable to inverting an altered exon 7 and delete the functioning exon 7.

In some embodiments, the recombinase is Cre. In some embodiments, the SRRS's are lox sites or variants thereof which are recognized by Cre. In some embodiments, a recombinase (e.g., Cre) is fused to a ligand binding domain responsive to binding by a ligand, e.g., Cre-ER$^{T2}$ which is responsive to (i.e., activated by) binding by tamoxifen or a functional analogs/derivative thereof. In one embodiment, a gene encoding CreER$^{T2}$ is integrated into the ROSA26 locus of a rodent genome.

In a further aspect, disclosed herein is an isolated rodent tissue or cell whose genome comprises a nucleic acid described above, i.e., the genome of the tissue or cell comprises a modified rodent Acvr1 gene. In some embodiments, an isolated rodent tissue or cell comprises a modified Acvr1 gene within an endogenous rodent Acvr1 locus. In some embodiments, the isolated rodent cell is an embryonic stem (ES) cell. In some embodiments, an isolated rodent tissue or cell is a rodent egg or a rodent embryo. The isolated rodent tissue or cell include, for example, mouse or rat tissue or cell.

In some embodiments, an isolated rodent tissue or cell comprises in its genome a modified rodent Acvr1 gene comprising a functioning Acvr1 exon 7 in sense orientation and flanked upstream and downstream by a first pair of SRRS', and an altered Acvr1 exon 7 in antisense orientation and flanked upstream and downstream by a second pair of SRRS', wherein the first and second pairs of SRRS' are orientated such that a recombinase can invert the altered Acvr1 exon 7 into sense orientation, and delete the functioning Acvr1 exon 7. In various embodiments, except for exon 7, the remaining exons of a modified rodent Acvr1 gene are functioning exons of an endogenous rodent Acvr1 gene, e.g., wild type exons present at an endogenous rodent Acvr1 locus.

In some embodiments, an isolated rodent tissue or cell comprises in its genome a modified rodent Acvr1 gene comprising (a) a functioning Acvr1 exon 7 encoding R258 in sense orientation, flanked upstream and downstream by a first pair of SRRS'; and (b) an altered rodent Acvr1 exon 7 encoding a R258G variation in antisense orientation, flanked by a second pair of SRRS' that are different from the first pair of SRRS'; wherein the first and second pairs of SRRS' are oriented so that a recombinase can invert the altered rodent Acvr1 exon 7 into sense orientation, delete the functioning Acvr1 exon 7, and allow an altered Acvr1 allele comprising the altered rodent Acvr1 exon 7 to be expressed. In some embodiments, expression of an altered Acvr1 allele comprising the altered rodent Acvr1 exon 7 results in ectopic bone formation. In various embodiments, except for exon 7, the remaining exons of a modified rodent Acvr1 gene are functioning exons of an endogenous rodent Acvr1 gene, e.g., wild type exons present at an endogenous rodent Acvr1 locus.

In some embodiments, a functioning Acvr1 exon 7 encoding R258 is a wild type rodent Acvr1 exon 7. In some embodiments, a functioning Acvr1 exon 7 encoding R258 is a substantially human ACVR1 exon 7. In some embodiments, a substantially human ACVR1 exon 7 is a wild type human ACVR1 exon 7. In other embodiments, a substantially human ACVR1 exon 7 differs from a wild type human ACVR1 exon 7 by at least one nucleotide and has a reduced sequence identity with an altered rodent Acvr1 exon 7 as compared to the sequence identity between the wild type human ACVR1 exon 7 and the altered rodent Acvr1 exon 7. In some embodiments, a substantially human ACVR1 exon 7 encodes the same amino acids as a wild type human ACVR1 exon 7.

In some embodiments, the first pair of SRRS' includes a first SRRS and a second SRRS, wherein the first and second SRRS' are compatible with each other and are oriented to direct an inversion. In some embodiments, the second pair of SRRS' includes a third SRRS and a fourth SRRS, wherein the third and fourth SRRS' are compatible with each other, are oriented to direct an inversion, but are not compatible with the first or second SRRS.

In some embodiments, an isolated rodent tissue or cell comprises in its genome a modified rodent Acvr1 gene comprising, with respect to the direction of transcription of the Acvr1 gene, (i) a functioning exon 7 (e.g., a substantially human exon 7) in sense orientation, and (ii) an altered exon 7 in antisense orientation; and comprises a first pair of SRRS' composed of a first SRRS (SRRS1) and a second SRRS (SRRS2), and a second pair of SRRS' composed of a third SRRS (SRRS3) and a fourth SRRS (SRRS4); wherein SRRS1 is compatible with SRRS2, SRRS3 is compatible with SRRS4, but neither SRRS1 nor SRRS2 is compatible with SRRS3 or SRRS4, wherein SRRS1 is located upstream of the functioning exon 7, SRRS2 is located just downstream (with respect to transcriptional direction of the Acvr1 gene) of the antisense altered exon 7, wherein SRRS1 and SRRS2 are oriented to direct an inversion; wherein SRRS3 is disposed between the functioning exon 7 and the altered antisense exon 7, and SRRS4 is located downstream (with respect to the direction of orientation of the Acvr1 gene) of SRRS2, wherein SRRS3 and SRRS4 are oriented to direct an inversion. In some embodiments, each of SRRS' 1-4 is recognized by the same recombinase, such as Cre.

In a further aspect, disclosed herein is a nucleic acid construct for targeted modification of an Acvr1 gene in a rodent genome, also referred to as "a targeting nucleic acid".

In some embodiments, a targeting nucleic acid comprises (a) a functioning Acvr1 exon 7 encoding R258 in sense orientation, flanked upstream and downstream by a first pair of SRRS'; and (b) an altered rodent Acvr1 exon 7 encoding a R258G variation in antisense orientation, flanked by a second pair of SRRS' that are different from the first pair of SRRS'; wherein the first and second pairs of SRRS' are oriented so that a recombinase can invert the altered rodent Acvr1 exon 7 into sense orientation and delete the functioning Acvr1 exon 7. In some embodiments, the functioning exon 7 and the altered exon 7 are each flanked by intronic sequences. Typically a targeting nucleic acid construct comprises 5' and 3' homology arms (nucleotide sequences homologous to the nucleotide sequences at the locus to be targeted) that mediate homologous recombination and integration of the nucleic acid sequence between the homology arms. In some embodiments, a targeting nucleic acid construct also comprises a selection marker gene to facilitate identification and selection of correctly targeted clones.

In some embodiments, a functioning Acvr1 exon 7 encoding R258 is a wild type rodent Acvr1 exon 7. In some embodiments, a functioning Acvr1 exon 7 encoding R258 is a substantially human ACVR1 exon 7. In some embodiments, a substantially human ACVR1 exon 7 is a wild type human ACVR1 exon 7. In other embodiments, a substantially human ACVR1 exon 7 differs from a wild type human ACVR1 exon 7 by at least one nucleotide and has a reduced sequence identity with an altered rodent Acvr1 exon 7 as compared to the sequence identity between the wild type human ACVR1 exon 7 and the altered rodent Acvr1 exon 7. In some embodiments, a substantially human ACVR1 exon 7 encodes the same amino acids as a wild type human ACVR1 exon 7.

In some embodiments, the first pair of SRRS' includes a first SRRS and a second SRRS, wherein the first and second SRRS' are compatible with each other and are oriented to direct an inversion. In some embodiments, the second pair of SRRS' includes a third SRRS and a fourth SRRS, wherein the third and fourth SRRS' are compatible with each other, are oriented to direct an inversion, but are not compatible with the first or second SRRS.

In some embodiments, a targeting nucleic acid comprises, with respect to the direction of transcription of the Acvr1 gene, (i) a functioning exon 7 (e.g., a substantially human exon 7) in sense orientation, and (ii) an altered exon 7 in antisense orientation; and comprises a first pair of SRRS' composed of a first SRRS (SRRS1) and a second SRRS (SRRS2), and a second pair of SRRS' composed of a third SRRS (SRRS3) and a fourth SRRS (SRRS4); wherein SRRS1 is compatible with SRRS2, SRRS3 is compatible with SRRS4, but neither SRRS1 nor SRRS2 is compatible with SRRS3 or SRRS4, wherein SRRS1 is located upstream of the functioning exon 7, SRRS2 is located just downstream (with respect to transcriptional direction of the Acvr1 gene) of the antisense altered exon 7, wherein SRRS1 and SRRS2 are oriented to direct an inversion; wherein SRRS3 is disposed between the functioning exon 7 and the altered antisense exon 7, and SRRS4 is located downstream (with respect to the direction of orientation of the Acvr1 gene) of SRRS2, wherein SRRS3 and SRRS4 are oriented to direct an inversion. In some embodiments, each of SRRS' 1-4 is recognized by the same recombinase, such as Cre.

In another aspect, disclosed herein is a method of making a genetically modified rodent, comprising modifying a rodent genome to comprise a modified rodent Acvr1 gene within an endogenous rodent Acvr1 locus as described herein.

In some embodiments, the rodent genome is modified by a process comprising introducing into a rodent embryonic stem (ES) cell a targeting nucleic acid construct described herein; obtaining a rodent ES cell whose genome comprises a modified rodent Acvr1 gene; and making a genetically modified rodent by using the rodent ES cell comprising a modified genome. For example, a targeting nucleic acid is introduced into a rodent ES cell, wherein the targeting nucleic acid comprises (a) a functioning Acvr1 exon 7 encoding R258 in sense orientation, flanked upstream and downstream by a first pair of SRRS'; and (b) an altered rodent Acvr1 exon 7 encoding a R258G variation in antisense orientation, flanked by a second pair of SRRS' that are different from the first pair of SRRS'; wherein the first and second pairs of SRRS' are oriented so that a recombinase can invert the altered rodent Acvr1 exon 7 into sense orientation and delete the functioning Acvr1 exon 7. A rodent ES cell can be selected whose genome has been modified and comprises the functioning Acvr1 exon 7 encoding R258 in sense orientation, flanked upstream and downstream by a first pair of SRRS'; and the altered rodent Acvr1 exon 7 encoding a R258G variation in antisense orientation, flanked by a second pair of SRRS' that are different from the first pair of SRRS'. Such rodent ES cell can be used to make a rodent.

In some embodiments, a genetically modified rodent made by the present method and comprising a modified rodent Acvr1 gene further comprises an inducible recombinase (e.g., Cre). In some embodiments, a nucleic acid encoding an inducible recombinase is present in the genome of a rodent ES cell into which a targeting nucleic acid construct is introduced. In some embodiments, a rodent comprising a modified rodent Acvr1 gene in its genome is made first and then crossed with another rodent comprising a nucleic acid encoding an inducible recombinase in its genome.

In some embodiments, the inducible recombinase is activated in a rodent and acts to invert an altered exon 7 and delete the functioning exon to allow an Acvr1 protein comprising an alteration (e.g., R258G) to be expressed.

In a further aspect, disclosed herein is a method of breeding rodents and rodent progenies obtained.

In some embodiments, disclosed herein is a method comprising breeding a first rodent whose genome comprises a modified rodent Acvr1 gene with a second rodent, resulting in a progeny rodent whose genome comprises the modified rodent Acvr1 gene. A modified rodent Acvr1 gene has been described herein; for example, a modified rodent Acvr1 gene may comprise a functioning Acvr1 exon 7 in sense orientation and flanked upstream and downstream by a first pair of SRRS', and an altered rodent Acvr1 exon 7 in antisense orientation and flanked upstream and downstream by a second pair of SRRS', wherein the first and second pairs of SRRS' are orientated such that a recombinase can invert the altered Acvr1 exon 7 into sense orientation, and delete the functioning Acvr1 exon 7. In some embodiments, an altered rodent Acvr1 exon 7 encodes a R258G variation, and a functioning Acvr1 exon 7 is a substantially human ACVR1 exon 7 encoding R258.

In some embodiments, the second rodent comprises an inducible recombinase. In some embodiments, the inducible recombinase is an inducible Cre recombinase. In some embodiments, an inducible Cre recombinase is a Cre-ER$^{T2}$ recombinase, inducible by binding of a ligand such as tamoxifen or a functional derivative or analog thereof.

In some embodiments, the progeny rodent comprises an inducible recombinase. In some embodiments, the inducible recombinase is an inducible Cre recombinase. In some embodiments, an inducible Cre recombinase is a Cre-ER$^{T2}$ recombinase, In some embodiments, the inducible recombinase is expressed in a cell or tissue, e.g., selected cells or tissues of the progeny rodent. In some embodiments, the expressed recombinase acts in a cell or tissue to invert the altered Acvr1 exon 7 into sense orientation and to delete the functioning Acvr1 exon 7, thereby allowing an altered Acvr1 allele comprising the altered exon 7 to be expressed.

Also provided herein are progeny rodents obtained from a breeding method disclosed herein.

In still another aspect, a genetically modified rodent animal that expresses an altered Acvr1 allele is used as a model for an ectopic ossification disorder. In one embodiment, the ectopic ossification disorder is fibrodysplasia ossificans progressiva (FOP). In some embodiments, a genetically modified rodent animal that expresses an altered Acvr1 allele is used to evaluate a candidate therapeutic compound for determining whether the candidate compound can inhibit the development of ectopic bone formation in the rodent.

DETAILED DESCRIPTION

Figure 1:
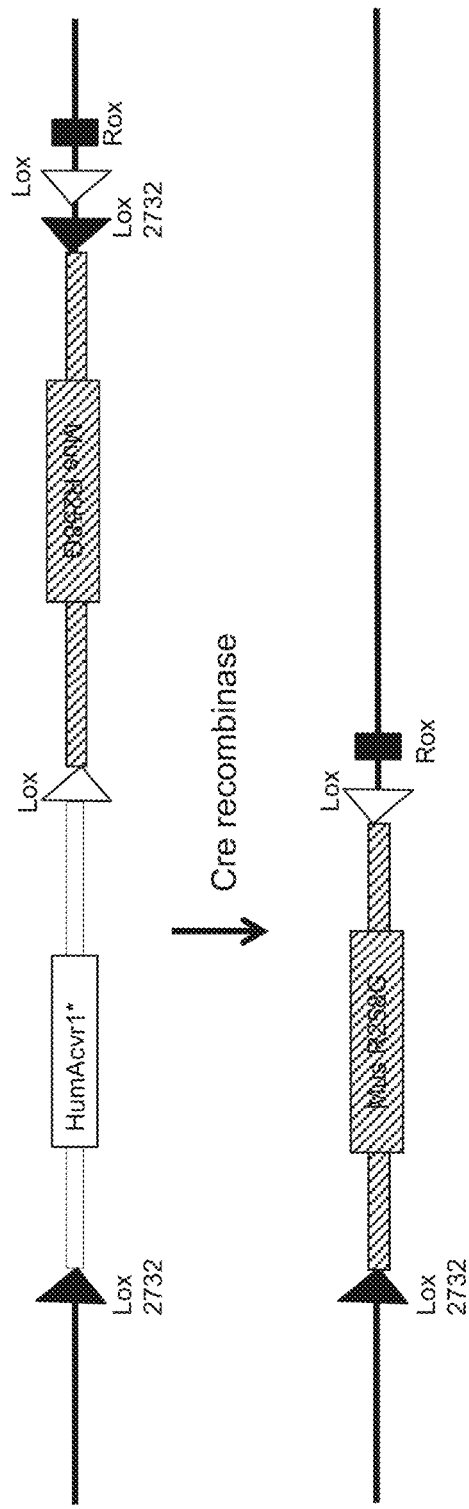
FIG. 1 illustrates the Acvr1 wild type to R258G FlEx schematics. The top schematic shows the Acvr1 genomic region after knockin and Neo deletion. The bottom schematic shows the genomic region after Cre-mediated inversion and deletion, which places the mutant exon in its normal location and orientation. The human exon (open box) and flanking intronic (open bar) sequences were used to reduce hairpin formation with the inverted mouse exon/intron (striped box/striped bar) sequences during transcription. Additional nucleotide changes were made to the human exon to further reduce sequence identity with the mouse exon.

Fibrodysplasia ossificans progressiva (FOP) is an autosomal dominant disorder of ectopic bone formation. Approximately 95% of FOP is caused by the R206H mutation in activin A type I receptor (Acvr1). However, several other mutations in either the GS or kinase domains, including R258G, have been reported to cause atypical FOP with a more severe phenotype. The two patients with the R258G mutation have profound developmental abnormalities in addition to developing heterotopic ossification after birth (Kaplan et al., Am J Med Genet A. 2015; 167(10): 2265-2271).

Genetically modified rodents are provided that are capable of expressing an Acvr1 protein comprising an alteration that results in a disorder characterized by ectopic bone formation, e.g., FOP. In some embodiments, rodents expressing the altered Acvr1 protein include rodents that are not chimeric, e.g., rodents whose genomes carry a modified Acvr1 gene comprising a conditional alteration that, once expressed, results in ectopic bone formation in a rodent.

Genetically modified rodents are provided that comprise a FlEx design that provides for a conditional deletion of a functioning exon and replacement of the functioning exon with an altered exon. A functioning exon encodes amino acids of a protein that is functional, i.e., performs its expected biological function. In some embodiments, a functioning exon is a naturally occurring, wild type exon. In some embodiments, a functioning exon encodes the same amino acids as a wild type exon. FlEx allows for forming a conditional allele by placement of a nucleic acid sequence encoding an altered exon in the antisense strand (hereon referred to as "inverted altered exon") next to a functioning exon that will later on be deleted. By utilizing selected site-specific recombinase recognition sites (SRRS's), in the presence of their cognate recombinase, the inverted altered exon is brought to the sense strand, and hence also in frame with the rest of the gene, whereas the functioning exon is deleted. This FlEx approach relies on the placement of incompatible SRRS's (e.g., lox2372 and loxP) surrounding the functioning and altered exons. Thus, one advantage of the FlEx approach is that a (perinatal/embryonic) lethal mutation is not expressed unless the FlEx allele is acted upon by the selected recombinase(s). Another advantage of this FlEx approach is permanent removal of the functioning exon upon exposure to the selected recombinase, and thus no inverted repeat remains in the genome post-inversion, which eliminates the possibility of regenerating a wild type allele. Yet another advantage of the FlEx approach is the permanent fixing of the altered exon in the sense strand which results from the removal of one of each of the two different types of SRRSs (e.g. one of the two lox2372 sites and one of the loxP sites). A functioning exon derived by humanization of a wild-type rodent exon also minimizes inverted repeat sequence, thus facilitating cloning steps and alleviating concerns of rearrangements during and after targeting, as well as RNA splicing artifacts during maturation of the corresponding mRNA. In some embodiments, a substantially human wild type exon is used in a FlEx design. The "human wild type exon" or "human exon" refers to a naturally occurring, functioning exon from human. The term "substantially human wild type exon" or "substantially human exon" include both a naturally occurring, functioning human exon, and modified forms thereof where one or more (e.g., 1, 2, 3, 4, 5, 6, 7, 8, 9, 10, 11, 12, 13, 14, 15 or more) nucleotides of a naturally occurring human exon have been altered. In specific embodiments, one or more (e.g., 1, 2, 3, 4, 5, 6, 7, 8, 9, 10, 11, 12, 13, 14, 15 or more) nucleotides have been altered without changing the encoded amino acids (essentially altered codon choices), to reduce sequence identity with the rodent exon, which further minimizes inverted repeat sequence and reduces the possibility of rearrangements.

If a rodent bearing a FlEx allele is bred to a recombinase-containing rodent, the altered allele will be expressed in the progeny in utero; and if the alteration is a perinatal/embryonic lethal alteration, the goal of making an animal that can be studied which expresses the allele may be compromised. Therefore, the rodent bearing a FlEx allele is not bred with an unregulated recombinase-containing rodent. Instead, the rodent bearing a FlEx allele is bred with a rodent that expresses a recombinase, the activity of which is inducible (e.g., responsive to an inducer) (i.e., an inducible recombinase). Inducible recombinases can be made by fusing a recombinase with a ligand binding domain of a protein that, when bound to its cognate ligand or functional derivatives of the cognate ligand, renders the protein functional (e.g., by stabilizing the protein). Functional derivatives of a cognate ligand refer to compounds that are analogous in structure and perform substantially the same function (i.e., binding to the same receptor) as the cognate ligand. Examples of such ligand-binding domains include, but are not limited to, the ligand-binding domains of steroid receptors, glucocorticoid receptors, retinoid receptors and thyroid receptors (Eilers et al. (1989) Nature 340:66-68; Picard et al. (1988) Cell 54:1073-1080). In some embodiments, an inducible recombinase is a fusion protein between Cre and an estrogen receptor (ER) modified with T2 mutations (encoded by a Cre-ER$^{T2}$ allele). With this fusion protein, the Cre recombinase is inactive in the absence of a ligand for the ER (see, Indra, A. et al. (1999), Nucleic Acids Res. 27(22):4324-4327; Feil, R. et al. (1997) Biochem. Biophys. Res. Commun. 237:752-757; U.S. Pat. No. 7,112,715), and the Cre recombinase becomes active when provided with a ligand for the ER, e.g., tamoxifen, or a functional derivative of tamoxifen. A rodent comprising a conditional allele constructed with Cre-responsive SRRS's as described herein, and containing a Cre-ER$^{T2}$ allele, would therefore express the allele comprising the functioning exon, unless and until the rodent is exposed to a ligand for the ER to induce Cre activity. In this way, rodents are generated that contain a modified Acvr1 gene in their germline but that do not express the corresponding variant Acvr1 protein unless and until the rodents are exposed to a ligand of the ER (e.g., tamoxifen). Following exposure to the ligand, the Cre-ER$^{T2}$ fusion protein is activated and the conditional allele is converted to the corresponding altered allele.

A ligand can be administered to the rodent via various routes to induce the activity of the recombinase, including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. In specific embodiments, a ligand is administered to a rodent via intraperitoneal injection.

In various embodiments, the conversion to an altered allele is irreversible, with deletion of the functioning exon. In this manner, a rodent line containing an otherwise lethal Acvr1 mutation can be maintained essentially indefinitely, producing the desired genetic lesion and accompanying phenotype whenever desired.

The rodents provided herein include, for example, mice, rats, and hamsters. In some embodiments, the rodent is a mouse or a rat. In specific embodiments, the rodent is a mouse. Acvr1 is highly conserved across species, with R258 being conserved and at the same position for mice and rats.

In some embodiments, the rodent is a mouse of a C57BL strain, for example, a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In other embodiments, the rodent is a mouse of a 129 strain, for example, a 129 strain selected from the group consisting of 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al. (1999), *Mammalian Genome* 10:836; Auerbach et al. (2000), *Biotechniques* 29(5):1024-1028, 1030, 1032). In some embodiments, the rodent is a mouse that is a mix of an aforementioned 129 strain and an aforementioned C57BL/6 strain. In certain embodiments, the mouse is a mix (i.e., hybrid) of aforementioned 129 strains, or a mix of aforementioned C57BL strains, or a mix of a C57BL strain and a 129 strain. In certain embodiments, the mouse is a mix of a C57BL/6 strain with a 129 strain. In specific embodiments, the mouse is a VGF1 strain, also known as F1H4, which is a hybrid of C57BL/6 and 129. In other embodiments, the mouse is a BALB strain, e.g., BALB/c strain. In some embodiments, the mouse is a mix of a BALB strain and another aforementioned strain.

In some embodiments, the rodent is a rat. In certain embodiments, the rat is selected from a Wistar rat, an LEA strain, a Sprague Dawley strain, a Fischer strain, F344, F6, and Dark Agouti. In other embodiments, the rat is a mix of two or more strains selected from the group consisting of Wistar, LEA, Sprague Dawley, Fischer, F344, F6, and Dark Agouti.

A conditional Acvr1 allele comprising the R258G variation can be engineered by utilizing the FlEx method. See, e.g., Schnutgen, F. et al. (2003) Nat. Biotech. 21:562-565; and U.S. Pat. No. 7,205,148. FlEx employs a pair of mutant Lox sites—referred to as a FlEx array—that are recognized by the same recombinase (Cre) but that do not react with one another, and are laid out in an A-B/[A-B] configuration, where the "[A-B]" is in the opposite strand with respect to "A-B", to enable inversion of the DNA sequence flanked by the arrays. In some embodiments, the pair of LoxP-Lox2372 is used as the combination of mutant Lox sites for the conditional allele described herein. These two mutant Lox sites do not exhibit cross-reactivity. The sequence that is contained within each array—i.e., between the LoxP and Lox2372 sites of each array—will be deleted upon action by Cre. One embodiment of a conditional allele is illustrated in FIG. 1.

Mouse Acvr1 displays a variety of splice variants (e.g., Acvr1-201, 202, 203, 204). The exons which are mutated in FOP, are shared by all protein-coding splice variants of Acvr1. In one embodiment, disclosed herein is a conditional Acvr1 allele comprising a modification of exon 7 (ENSMUSE00001232449) of the isoform, Acvr1-201.

An Acvr1$^{[R258G]FlEx}$ allele can be engineered by placing the altered version of the amino acid 258-encoding exon of rodent Acvr1 (e.g., ENSMUSE00001232449) in the antisense strand, so that the altered exon is not incorporated into Acvr1's transcript. As the sequence encoded by exon 7 is required for Acvr1 function, this necessitated that a functioning exon 7 is also incorporated into the design (exon 7 is shared by all protein-coding splice variants of Acvr1). Furthermore, since exons are not recognized as such without accessory intronic sequences, both upstream and downstream sequences of the exon are also incorporated into both an altered and functioning amino acid 258-encoding exons. However, doing so would generate a large inverted repeat, and such DNA structures are inherently prone to recombination both during the genetic engineering steps required to build the targeting vector as well as post-targeting, in vivo (Holkers, M. et al. (2012) Nucleic Acids Res. 40:1984-1999). Furthermore, if the wild type rodent sequence of the amino acid 258-encoding exon and the upstream and downstream intronic sequences associated with the exon were retained intact and precede the altered rodent exon, then this wild type region could act as a homology arm and be utilized during targeting in the rodent ES cells, thereby resulting in exclusion of the altered exon from the targeted allele.

Therefore, an Acvr1$^{[R258G]FlEx}$ allele can be designed in a manner such that:

a) A large inverted repeat is avoided. To accomplish this, the R258-encoding exon (e.g., ENSMUSE00001232449) as well associated upstream and downstream intronic sequences can be replaced with the corresponding region from human ACVR1.

b) The wild type rodent sequence of the R258-encoding exon (e.g., ENSMUSE00001232449) is preserved at the protein level. The mouse and human protein sequences encoded by exons ENSMUSE00001232449 and ENSE00001009617, respectively, are identical. However, where possible, the codons within the human exon sequence (e.g., ENSE00001009617) can be altered to further reduce the nucleotide sequence identity between the rodent and human exons, without altering the amino acids encoded by the exon.

c) The introduced human sequence is removed in its entirety upon action by Cre.

Therefore, in the "conditional-on" state—where the Acvr1$^{[R258G]}$ mutant gene is transcribed—no human sequences remain and hence any resulting phenotype cannot be attributed to the presence of extraneous sequence.

More specifically, as an example, the region bounded by nucleotides 58468399 to 58468770 in mmuAcvr1 (i.e., nucleotides 58468399 to 58468770 of mouse Chromosome 2, GRCm38/mm10) was replaced with a nucleic acid composed of nucleotides 157770252 to 157770625 of hsaACVR1 (i.e., nucleotides 157770252 to 157770625 of human Chromosome 2, GRCh38/hg38), in a manner such that the introduced sequence, which includes hsaACVR1 exon ENSE00001009617, was transcribed as part of the resulting modified Acvr1$^{[R258G]FlEx}$ locus. In addition, by altering codon choice, the nucleotide sequence of human exon ENSE00001009617 was altered to reduce sequence identity between the mouse and human exon, without altering protein coding. This introduced human sequence is referred to hereafter as hsa_e7+. Therefore, prior to inversion of the FlEx element (altered exon ENSMUSE00001232449 and associated upstream and downstream intronic sequences—see below), the resulting locus, Acvr1$^{[R258G]FlEx}$ should function as wild type.

The R258G variation was modeled by altering exon ENSMUSE00001232449 in the corresponding position, through altering the codon defined by nucleotides 58468530 to 58468532 from AGG (coding for arginine) to GGG (coding for glycine). The resulting mutant exon, along with flanking intronic sequences, were placed 3' to hsa_e7+ and in the antisense strand of mmuAcvr1. In addition, nucleotides 58468771-58468815 of mmuAcvr1 were deleted in order to create a small deletion that would accommodate LOA probes (Gomez-Rodriguez, J. et al. (2008) Nucleic Acids Res. 36:e117; Valenzuela, D. et al. (2003) High-throughput engineering of the mouse genome coupled with high-resolution expression analysis, Nat. Biotech. 21:652-659). This introduced mutated mouse sequence is hereafter referred to as mmu_e7R258G+.

Exemplary sequences of human exon 7, altered mouse exon 7 encoding R258G, and altered human exon 7, along with upstream and downstream intronic sequences are summarized below and set forth in the Sequence Listing.

| SEQ ID NO | Description |
| --- | --- |
| 1 | Human exon 7 |
| 2 | Human exon 7 with codon alterations |
| 3 | Human sequence including codon altered exon 7 and surrounding introns |
| 4 | Mouse altered exon 7 encoding R258G |
| 5 | Mouse altered exon 7 (in reverse as in construct) |
| 6 | Mouse sequence including altered exon 7 and surrounding introns |
| 7 | Mouse sequence including altered exon 7 and surrounding introns (in reverse as in construct) |
| 8 | Rat exon 7 |

In order to enable Cre-dependent inversion of the mmu_e7R258G+ and simultaneous deletion of hsa_e7+, a combination of FlEx like Lox arrays were used such that:
  a) hsa_e7+ is preceded by a LoxP site, and followed by a Lox2372 site. In this respect, hsa_e7+ is contained with the 5' LoxP-Lox2372 FlEx-like array.
  b) mmu_e7R258G+ is followed by the 3' LoxP-Lox2372 FlEx-like array, but this array is engineered such that it is in a mirror image configuration to the 5' LoxP-Lox2372 FlEx-like array. This enables permanent inversion of mmu_e7R258G+ into the sense strand by Cre.

When the resulting allele, $Acvr1^{[R258G]FlEx}$, is exposed to Cre, the hsa_e7+ will be deleted and the mmu_e7R258G+ will be inverted into the sense strand. As a result, $Acvr1^{[R258G]}$ will be expressed in place of Acvr1.

A targeting nucleic acid construct comprising an Acvr1 FlEx allele described above can be made for introducing the Acvr1 FlEx allele into a rodent genome. In addition to an Acvr1 FlEx sequence (a substantially human exon 7 in sense orientation and surrounding intronic sequences, an altered rodent exon 7 encoding R258G in antisense orientation and surrounding intronic sequences, and recombination recognition sites), the nucleic acid construct can include flanking sequences that are of suitable lengths and homologous to rodent Acvr1 gene sequences at an endogenous rodent Acvr1 locus so as to be capable of mediating homologous recombination and integration of the Acvr1 FlEx sequence into the endogenous rodent Acvr1 locus.

In some embodiments, a targeting nucleic acid construct comprising a Acvr1 FlEx allele is introduced into a rodent embryonic stem (ES) cell to modify the genome of the ES cell. Both mouse ES cells and rat ES cells have been described in the art. See, e.g., U.S. Pat. Nos. 7,576,259, 7,659,442, and 7,294,754, and US Publ. No. 2008/0078000 A1 (all of which are incorporated herein by reference) describe mouse ES cells and the VELOCIMOUSE® method for making a genetically modified mouse; and US Publ. No. 2014/0235933 A1 and US Publ. No. 2014/0310828 A1 (all of which are incorporated herein by reference) describe rat ES cells and methods for making a genetically modified rat.

ES cells having an Acvr1 FlEx allele integrated in the endogenous rodent Acvr1 locus can be selected. ES cells having an Acvr1 FlEx allele integrated in the genome are then used as donor ES cells for injection into a pre-morula stage embryo (e.g., 8-cell stage embryo) by using the VELOCIMOUSE® method (see, e.g., U.S. Pat. Nos. 7,576,259, 7,659,442, and 7,294,754, and US Publ. No. 2008/0078000 A1), or methods described in US Publ. Nos. 2014/0235933 A1 and 2014/0310828 A1. The embryo comprising the donor ES cells is incubated until blastocyst stage and then implanted into a surrogate mother to produce an F0 rodent fully derived from the donor ES cells. Rodent pups bearing the FlEx allele can be identified by genotyping of DNA isolated from tail snips using, for example, a loss of allele assay (Valenzuela et al., supra).

In various embodiments, a genetically modified rodent comprising an Acvr1 FlEx allele is made by modifying a rodent ES cell to contain the FlEx allele, and modifying the same ES cell to contain a gene encoding an inducible recombinase (e.g., Cre-$ER^{T2}$), and using the ES cell as a donor cell to make a rodent that contains the FlEx allele and the gene encoding the inducible recombinase. In some embodiments, a genetically modified rodent comprising an Acvr1 FlEx allele is made by using a rodent ES cell that already comprises a gene encoding an inducible recombinase (e.g., Cre-$ER^{T2}$), and modifying such rodent ES cell to comprise an FlEx allele. In other embodiments, a genetically modified rodent comprising an Acvr1 FlEx allele is made and crossed with a rodent containing a gene encoding an inducible recombinase (e.g., Cre-$ER^{T2}$) to obtain an offspring that contains the FlEx allele and the gene encoding the inducible recombinase.

Figure 2:
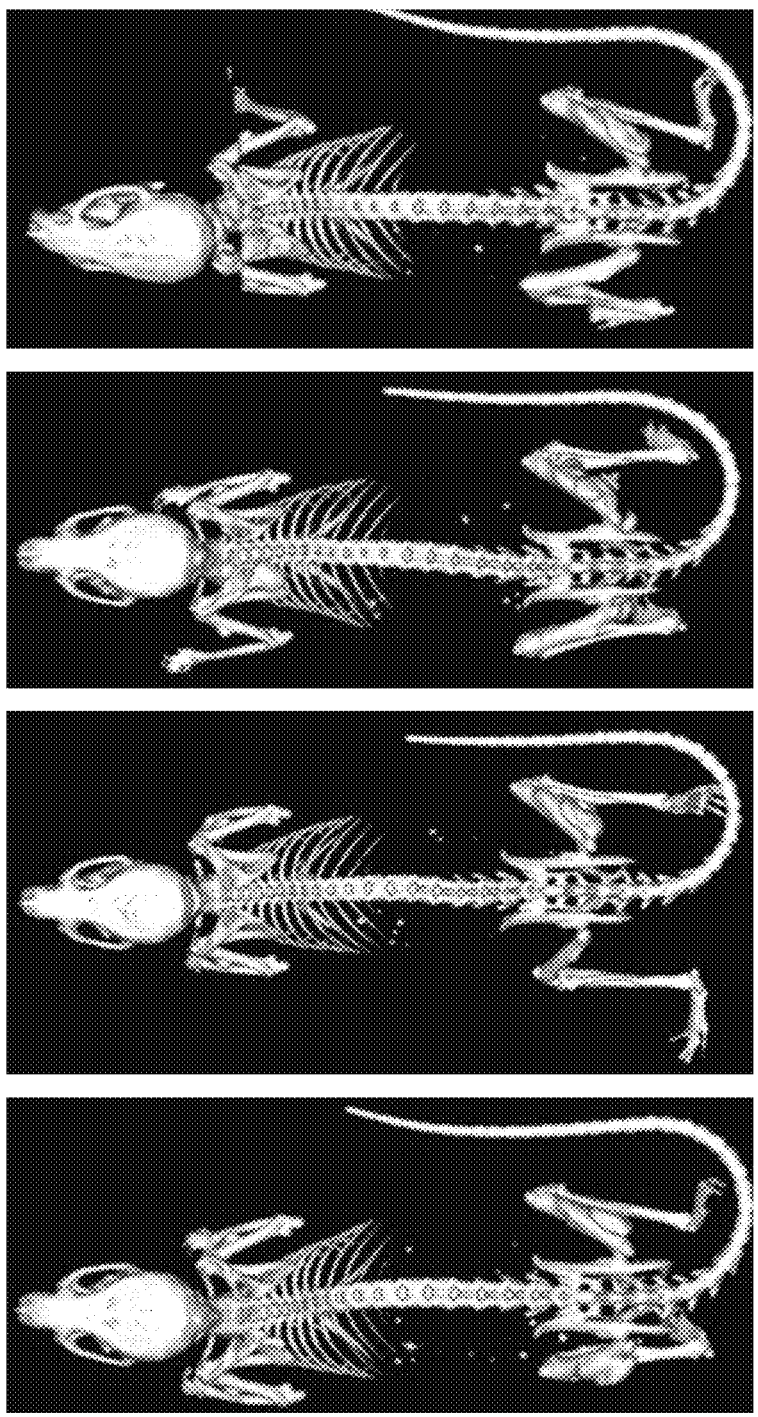
FIG. 2 shows that Acvr1$^{[R258G]FlEx/+}$; Gt(ROSA26)Sor$^{CreERt2/+}$ mice developed heterotopic ossification (HO) after tamoxifen treatment. Four Acvr1$^{[R258G]FlEx/+}$; Gt(ROSA26)Sor$^{CreERt2/+}$ mice were given 5 daily 40 mg/kg tamoxifen injections. After 2 weeks, all mice showed HO formation.

$Acvr1^{R258GFlEx/+}$; $Gt(ROSA26)Sor^{CreERt2/+}$ adult mice were phenotypically normal; however, body-wide activation of the R258G-encoding Acvr1 allele resulted in progressive ossification, evident radiographically as early as 2 weeks after dosing with tamoxifen, in a manner similar to that seen with the Acvr1 R206H Flex mouse described in U.S. Pat. No. 9,510,569. See also FIG. 2.

The rodents provided herein permit a better understanding of the molecular mechanisms underlying the development of ectopic bone disorders such as FOP. In addition, such rodents may be used in the screening and development of therapeutic compounds for the inhibition, prevention, and/or treatment of ectopic bone disorders, including FOP.

In some embodiments, a candidate therapeutic compound is tested in vivo, by administering the compound to a rodent disclosed herein, i.e., a rodent carrying an Acvr1 FlEx allele.

Candidate therapeutic compounds can be, without limitation, small molecule chemical compounds, antibodies, inhibitory nucleic acids, or any combination thereof. In a specific embodiment, the compound is an antibody or antigen-binding fragment thereof, e.g., an anti-Acvr1 antibody or antigen-binding fragment thereof. In some embodiments, the compound comprises an antagonist of one or more of activin receptor 1, activin receptor type 2A, and activin receptor type 2B. Any such antagonist may comprise an antibody. In some embodiments, the compound comprises an antibody against activin A. An antagonist or antibody against activin receptor 1, against activin receptor type 2A, against activin receptor type 2B, or against activin A may be any antagonist or antibody described or exemplified in U.S. Publ. No. 2018/0111983, which is incorporated by reference herein.

Administration of the compound can be performed before, during, or after induction of the recombinase activity in the rodent to allow the mutant Acvr1 allele to be expressed. Candidate therapeutic compounds may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection.

Various assays may be performed to determine the pharmacokinetic properties of administered compounds using samples obtained from rodent animals described. Pharmacokinetic properties include, but are not limited to, how a non-human animal processes the compound into various metabolites (or detection of the presence or absence of one or more metabolites, including, but not limited to, toxic metabolites), half-life, circulating levels (e.g., serum concentration), anti-compound response (e.g., antibodies), absorption and distribution, route of administration, routes of excretion and/or clearance of the compound.

In some embodiments, performing an assay includes determining the differences between a mutant rodent animal administered a compound and a mutant rodent animal not administered the compound, and determining whether the compound can inhibit the development and/or progression of ectopic bone formation in the rodent.

The present description is further illustrated by the following examples, which should not be construed as limiting in any way. The contents of all cited references (including literature references, issued patents, and published patent applications as cited throughout this application) are hereby expressly incorporated by reference.

Example 1

The region bounded by nucleotides 58468399 to 58468770 in mmuAcvr1 (i.e., nucleotides 58468399 to 58468770 of mouse Chromosome 2, GRCm38/mm10) was replaced with a nucleic acid composed of nucleotides 157770252 to 157770625 of hsaACVR1 (i.e., nucleotides 157770252 to 157770625 of human Chromosome 2, GRCh38/hg38), in a manner such that the introduced sequence, which includes hsaACVR1 exon ENSE00001009617, was transcribed as part of the resulting modified Acvr1$^{[R258G]FlEx}$ locus. In addition, by altering codon choice, the nucleotide sequence of human exon ENSE00001009617 was altered to reduce sequence identity between the mouse and human exon, without altering protein coding. This introduced human sequence is referred to hereafter as hsa_e7+. Therefore, prior to inversion of the FlEx element (altered exon ENSMUSE00001232449 and associated upstream and downstream intronic sequences—see below), the resulting locus, Acvr1$^{[R258G]FlEx}$, should function as wild type.

The R258G variation was modeled by altering exon ENSMUSE00001232449 in the corresponding position, through altering the codon defined by nucleotides 58468530 to 58468532 from AGG (coding for arginine) to GGG (coding for glycine). The resulting altered exon, along with flanking intronic sequences, were placed 3' to hsa_e7+ and in the antisense strand of mmuAcvr1. In addition, nucleotides 58468771-58468815 of mmuAcvr1 were deleted in order to create a small deletion that would accommodate LOA probes (Gomez-Rodriguez, J. et al. (2008) Nucleic Acids Res. 36:e117; Valenzuela, D. et al. (2003) High-throughput engineering of the mouse genome coupled with high-resolution expression analysis, Nat. Biotech. 21:652-659). This introduced mutated mouse sequence is hereafter referred to as mmu_e7R258G+.

In order to enable Cre-dependent inversion of the mmu_e7R258G+ and simultaneous deletion of hsa_e7+, a combination of FlEx like Lox arrays were used such that:
a) hsa_e7+ was preceded by a LoxP site, and followed by a Lox2372 site. In this respect, hsa_e7+ was contained with the 5' LoxP-Lox2372 FlEx-like array.
b) mmu_e7R258G+ was followed by the 3' LoxP-Lox2372 FlEx-like array, but this array was engineered such that it was in a mirror image configuration to the 5' LoxP-Lox2372 FlEx-like array. This enabled permanent inversion of mmu_e7R258G+ into the sense strand by Cre.

When the resulting allele, Acvr1$^{[R258G]FlEx}$ is exposed to Cre, the hsa_e7+ will be deleted and the mmu_e7R258G+ will be inverted into the sense strand. As a result, Acvr1$^{[R258G]}$ will be expressed in place of Acvr1.

Homozygous Acvr1$^{[R258G]FlEx/R258G]FlEx]}$ mice were born at an expected Mendalian ratio suggesting that splicing was normal in this mouse and wild type Acvr1 was being expressed.

Example 2

Inducing FOP in Acvr1$^{[R258G]/FlEx}$ Mice

To enable time-controlled yet whole body inversion of the Acvr1$^{[R258G]FlEx}$ allele, Acvr1$^{[R258G]FlEx}$ mice were mated with Gt(ROSA26)Sor$^{CreERT2/+}$ mice to generate Acvr1$^{[R258G]FlEx}$; Gt(ROSA26)Sor$^{CreERT2/+}$. These were maintained in heterozygosity on a mixed-C57BL/6NTac-129S6/SvEvTac background. All experiments were performed in accordance with the Institutional Animal Care and Use Committee of Regeneron. Both male and female mice were used between 8 and 11 weeks of age, however mice were aged and sex matched between groups. No age or sex related phenotypes were noted. The model was initiated by inversion of the R258G-encoding exon into the sense strand, which was accomplished by treating Acvr1$^{[R258G]FlEx}$; Gt(ROSA26)Sor$^{CreERT2/+}$ mice with 40 mg/kg of tamoxifen (Sigma) in oil intraperitoneally (i.p.) daily for 5 days (to activate CreER$^{T2}$). To assess heterotopic bone formation, mice were anesthetized by isofluorane and whole body-scanned, with a field of view at 60 mm×120 mm, using in vivo μCT (Quantum FX, PerkinElmer, Hopkinton, Mass., USA). The X-ray source was set to a current of 160 μA, voltage of 90 kVp, with a voxel size at 120 or 240 μm.

Acvr1$^{R258GFlEx/+}$; Gt(ROSA26)Sor$^{CreERt2/+}$ adult mice were phenotypically normal; however, body-wide activation of the R258G mutant Acvr1 allele resulted in progressive ossification, evident radiographically as early as 2 weeks after dosing with tamoxifen, in a manner similar to that seen with the Acvr1R206HFlex mouse described in U.S. Pat. No. 9,510,569. See also FIG. 2.

Antibody Dosing of Mice

For treatment studies, Acvr1$^{[R258G]FlEx/+}$; Rosa$^{CreERT2}$ mice were separated to ensure age and sex matching across groups, treatments were initiated on the same day as tamoxifen administration. Mice were injected subcutaneously (s.c.) with 25 mg/kg of either a neutralizing antibody generated against human Activin A (U.S. Patent Application 2015/0037339) or an isotype control antibody weekly for 6 weeks. Heterotopic bone formation was monitored weekly by in vivo μCT imaging.

Figure 3:
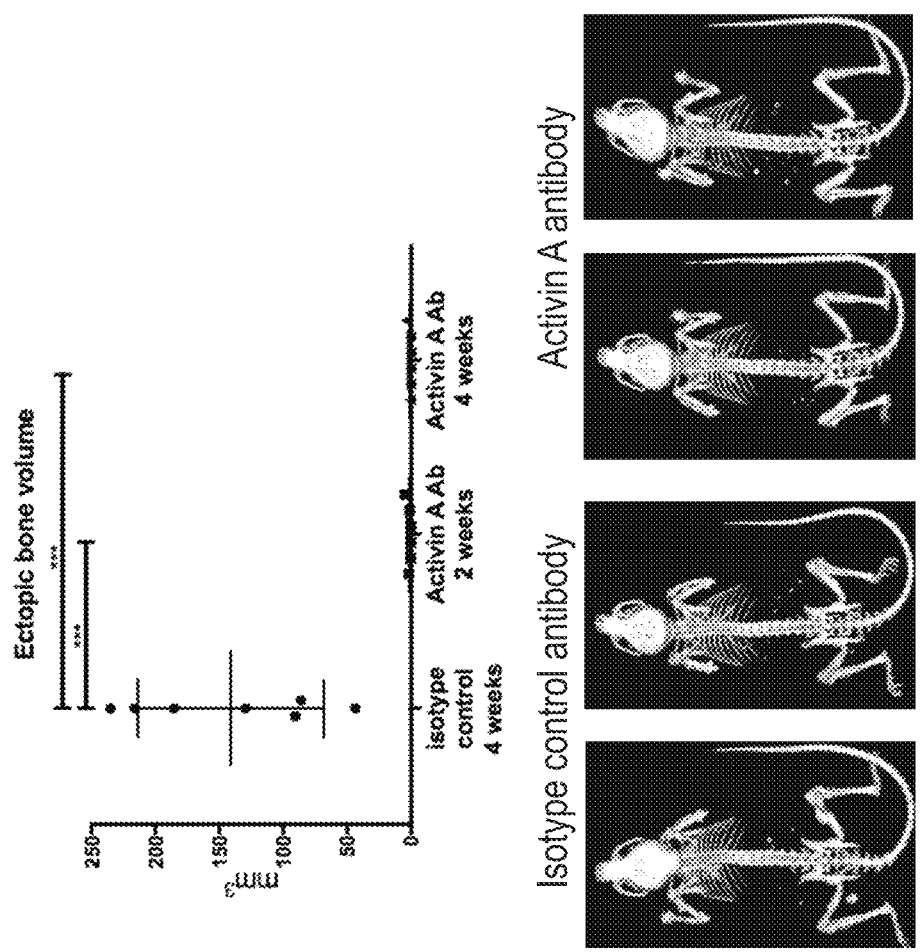
FIG. 3 shows that an anti-Activin A blocking antibody inhibits HO formation in Acvr1$^{R258G}$ conditional-on knock-in mice.

As shown in FIG. 3, mice receiving an isotype control antibody developed HO at 4 weeks, and mice receiving an Activin A blocking antibody had no detectable HO formation above μCT background after 4 weeks.

In summary, conditional-on knock-in alleles of ACVR1$^{R206H}$ or ACVR1$^{R258G}$ faithfully model Fibrodysplasia Ossificans Progressiva (FOP) in rodents such as mice; and an Activin A neutralizing antibody blocks the development of heterotopic ossification such rodent model.

Further Embodiments

1. A genetically modified rodent, whose genome comprises a modified rodent Acvr1 gene within an endogenous rodent Acvr1 locus, wherein the modified rodent Acvr1 gene comprises
   a) a substantially human ACVR1 exon 7 in sense orientation flanked by a first pair of site-specific recombinase recognition sites (SRRS'), wherein the substantially human ACVR1 exon 7 encodes the same amino acids as a human ACVR1 exon 7; and
   b) an altered rodent Acvr1 exon 7 encoding R258G in antisense orientation, flanked by a second pair of SRRS' that are different from the first pair of SRRS';
   wherein the first and second SRRS' are oriented so that a recombinase can invert the mutant rodent Acvr1 exon 7 into sense orientation, delete the substantially human ACVR1 exon 7, and allow an altered Acvr1 allele comprising the altered rodent Acvr1 exon 7 to be expressed.
2. The genetically modified rodent of item 1, wherein the substantially human ACVR1 exon 7 differs from the human ACVR1 exon 7 by at least one nucleotide and has a reduced sequence identity with the altered rodent Acvr1 exon 7 as compared to the sequence identity between the human ACVR1 exon 7 and the altered rodent Acvr1 exon 7.
3. The genetically modified rodent of item 1, wherein the gene encoding the recombinase is in the genome of the genetically modified rodent, and the activity of the recombinase is inducible.
4. The genetically modified rodent according to any one of items 1-3, wherein the recombinase is Cre.
5. The genetically modified rodent of item 4, wherein the Cre is fused to a ligand binding domain of an estrogen receptor (ER) such that the activity of the Cre is induced by ligand binding to the ER.
6. The genetically modified rodent of item 5, wherein the ligand binding domain of the ER comprises T2 mutations.
7. The genetically modified rodent of item 5 or 6, wherein the ligand is tamoxifen.
8. The genetically modified rodent of any one of items 1-7, wherein the genetically modified rodent is homozygous for the modified Acvr1 gene.
9. A mutant rodent derived from the genetically modified rodent of any of items 1-8, wherein the mutant rodent has a genome comprising an altered Acvr1 allele which comprises the altered exon 7 in sense orientation, and wherein the altered Acvr1 allele is expressed in the mutant rodent resulting in ectopic bone formation.
10. The rodent according to any of the preceding items, selected from a mouse or a rat.
11. A nucleic acid, comprising a modified rodent Acvr1 gene, wherein the modified rodent Acvr1 gene comprises
    a) a substantially human ACVR1 exon 7 in sense orientation flanked by a first pair of site-specific recombinase recognition sites (SRRS'), wherein the substantially human ACVR1 exon 7 encodes the same amino acids as a human ACVR1 exon 7; and
    b) an altered rodent Acvr1 exon 7 encoding R258G in antisense orientation, flanked by a second pair of SRRS' that are different from the first pair of SRRS';
    wherein the first and second SRRS' are oriented so that a recombinase can invert the mutant rodent Acvr1 exon 7 into sense orientation, delete the substantially human ACVR1 exon 7.
12. The nucleic acid of item 11, wherein the substantially human ACVR1 exon 7 differs from the human ACVR1 exon 7 by at least one nucleotide and has a reduced sequence identity with the altered rodent Acvr1 exon 7 as compared to the sequence identity between the human ACVR1 exon 7 and the altered rodent Acvr1 exon 7.
13. The nucleic acid of item 11, wherein the activity of the recombinase is inducible.
14. The nucleic acid of any one of items 11-13, wherein the recombinase is Cre.
15. The nucleic acid of item 14, wherein the Cre is fused to a ligand binding domain of an estrogen receptor (ER) such that the activity of Cre is induced by ligand binding to the ER.
16. The nucleic acid of item 15, wherein the ligand binding domain of the ER comprises T2 mutations.
17. The nucleic acid of item 15 or 16, wherein the ligand is tamoxifen.
18. The nucleic acid of any one of items 11-17, wherein the rodent is a mouse or a rat.
19. A rodent genome comprising the nucleic acid of item 11 or 12.
20. The rodent genome of item 19, further comprising a gene encoding the recombinase that recognizes the SRRS' and inverts the altered exon.
21. The rodent genome of item 20, wherein the activity of the recombinase is inducible.
22. The rodent genome of item 21, wherein the recombinase is Cre.
23. The rodent genome of item 22, wherein the Cre is fused to a ligand binding domain of an estrogen receptor (ER) such that the activity of the Cre is induced by ligand binding to the ER.
24. The rodent genome of item 23, wherein the ligand binding domain of the ER comprises T2 mutations.
25. The rodent genome of item 23 or 24, wherein the ligand is tamoxifen.
26. The rodent genome of any one of items 19-25, wherein the rodent genome is homozygous for for the modified Acvr1 gene.
27. The rodent genome of any one of items 19-26, wherein the rodent is a mouse or a rat.
28. An isolated rodent tissue or cell comprising the rodent genome of any one of items 19-27.
29. The isolated rodent tissue or cell of item 28, wherein the rodent is a mouse or a rat.
30. The isolated rodent tissue or cell of item 28 or 29, wherein the rodent cell is an embryonic stem cell.
31. A nucleic acid construct for targeted modification of an Acvr1 gene in a rodent genome, comprising:
    a) a substantially human ACVR1 exon 7 in sense orientation flanked by a first pair of site-specific recombinase recognition sites (SRRS'), wherein the substantially human ACVR1 exon 7 encodes the same amino acids as a human ACVR1 exon 7; and
    b) an altered rodent Acvr1 exon 7 encoding R258G in antisense orientation, flanked by a second pair of SRRS' that are different from the first pair of SRRS';
    wherein the first and second SRRS' are oriented so that a recombinase can invert the mutant rodent Acvr1 exon 7 into sense orientation, delete the substantially human ACVR1 exon 7, and allow an altered Acvr1 allele comprising the altered rodent Acvr1 exon 7 to be expressed.
32. The nucleic acid construct of item 31, wherein the substantially human ACVR1 exon 7 differs from the human ACVR1 exon 7 by at least one nucleotide and has a reduced sequence identity with the altered rodent Acvr1 exon 7 as compared to the sequence identity between the human ACVR1 exon 7 and the altered rodent Acvr1 exon 7.

33. The nucleic acid construct of item 31, wherein the first and second pairs of SRRS are Lox2372 and LoxP or vice versa.

34. The nucleic acid construct of item 31, wherein the recombinase is Cre.

35. The nucleic acid construct of item 34, wherein the Cre is fused to an estrogen receptor (ER) such that the activity of the Cre is induced by ligand binding to the ER.

36. The nucleic acid construct of item 35, wherein the ER comprises T2 mutations.

37. The nucleic acid construct of item 35, wherein the ligand is tamoxifen.

38. The nucleic acid construct according to any one of item 31-37, wherein the rodent is selected from a mouse or a rat.

39. A method of making a genetically modified rodent, comprising modifying a rodent genome to comprise a modified rodent Acvr1 gene within an endogenous rodent Acvr1 locus, wherein the modified rodent Acvr1 gene comprises
   a) a substantially human ACVR1 exon 7 in sense orientation flanked by a first pair of site-specific recombinase recognition sites (SRRS'), wherein the substantially human ACVR1 exon 7 encodes the same amino acids as a human ACVR1 exon 7; and
   b) an altered rodent Acvr1 exon 7 encoding R258G in antisense orientation, flanked by a second pair of SRRS' that are different from the first pair of SRRS';
   wherein the first and second SRRS' are oriented so that a recombinase can invert the altered rodent Acvr1 exon 7 into sense orientation, delete the substantially human ACVR1 exon 7, and allow an altered Acvr1 allele comprising the altered rodent Acvr1 exon 7 to be expressed.

40. The method of item 39, wherein the rodent genome is modified by a process comprising:
   a) introducing a nucleic acid construct into a rodent embryonic stem (ES) cell, wherein the nucleic acid construct comprises:
      the substantially human ACVR1 exon 7 in sense orientation flanked by the first pair of SRRS', and
      the altered rodent Acvr1 exon 7 encoding R258G in antisense orientation, flanked by the second pair of SRRS';
      wherein the nucleic acid construct targets the endogenous rodent Acvr1 locus resulting in the modified rodent Acvr1 gene within the endogenous rodent Acvr1 locus;
   b) obtaining a genetically modified rodent ES cell whose genome comprises the modified rodent Acvr1 gene; and
   c) making a genetically modified rodent by using the genetically modified rodent ES cell from b).

41. The method of item 39 or 40, wherein the genetically modified rodent is homozygous for the modified Acvr1 gene.

42. The method of item 40 or 41, wherein the rodent ES cell further comprises a gene encoding the recombinase.

43. The method of any one of items 39-42, wherein the activity of the recombinase is inducible.

44. The method according to any one of items 39-43, wherein the recombinase is Cre.

45. The method of item 44, wherein the Cre is fused to a ligand binding domain of an estrogen receptor (ER) such that the activity of the Cre is induced by ligand binding to the ER.

46. The method of item 45, wherein the ligand binding domain of the ER comprises T2 mutations.

47. The method of item 45 or 46, wherein the ligand is tamoxifen.

48. The method of any one of items 43-47, further comprising inducing the activity of the recombinase in a cell or tissue of the rodent, wherein the recombinase inverts the altered exon 7, deleting the substantially human exon 7, thereby allowing an altered Acvr1 allele comprising the altered exon 7 to be expressed in the cell or tissue.

49. The method according to any one of items 40-48, wherein the rodent is selected from a mouse or a rat.

50. A method of breeding, comprising breeding a first rodent whose genome comprises a modified rodent Acvr1 gene with a second mouse, resulting in a progeny rodent whose genome comprises the modified rodent Acvr1 gene, wherein the modified rodent Acvr1 gene comprises:
   a) a substantially human ACVR1 exon 7 in sense orientation flanked by a first pair of site-specific recombinase recognition sites (SRRS'), wherein the substantially human ACVR1 exon 7 encodes the same amino acids as a human ACVR1 exon 7; and
   b) an altered rodent Acvr1 exon 7 encoding R258G in antisense orientation, flanked by a second pair of SRRS' that are different from the first pair of SRRS';
   wherein the first and second SRRS' are oriented so that a recombinase can invert the altered rodent Acvr1 exon 7 into sense orientation, delete the substantially human ACVR1 exon 7, and allow an altered Acvr1 allele comprising the altered rodent Acvr1 exon 7 to be expressed.

51. The method of item 50, wherein the first rodent is homozygous for the modified rodent Acvr1 gene.

52. The method of item 50 or 51, wherein the second rodent comprises an inducible recombinase.

53. The method of item 52, wherein the inducible recombinanse is an inducible Cre recombinase.

54. The method of item 53, wherein the inducible Cre recombinase comprises a tamoxifen-inducible Cre-ER$^{T2}$ recombinase.

55. The method of any one of items 52-54, further comprising inducing the inducible recombinase in a cell or tissue in the progeny rodent, such that the induced recombinase inverts the altered rodent Acvr1 exon 7 into sense orientation and delete the substantially human ACVR1 exon 7 in the cell or tissue, thereby producing an altered Acvr1 allele comprising the altered rodent Acvr1 exon 7.

56. The method of any one of items 50-55, wherein the rodent is a mouse or a rat.

57. A progeny rodent produced according to the method of any one of items 50-56.

58. A method of testing a candidate therapeutic compound for treating ectopic bone formation, comprising:
   providing a genetically modified rodent according to any one of items 1-8 and 10;
   inducing the activity of the recombinase in the rodent to allow an altered Acvr1 allele comprising the altered rodent Acvr1 exon 7 to be expressed;
   administering the candidate compound to the rodent; and
   determining whether the candidate compound inhibits the development of ectopic bone formation in the rodent.

59. The method of item 58, wherein the candidate compound is administered to the rodent before, during, or after the induction of the recombinase activity.
60. The method of item 58, wherein the candidate compound is a small molecule chemical compound.
61. The method of item 58, wherein the candidate compound is a nucleic acid.
62. The method of item 58, wherein the candidate compound is an antibody or antigen-binding fragment thereof.
63. The method of item 62, wherein the antibody or antigen-binding fragment thereof is an antibody or antigen-binding fragment thereof against activin receptor 1.
64. The method of item 62, wherein the antibody or antigen-binding fragment thereof is an antibody or antigen-binding fragment thereof against activin receptor type 2A.
65. The method of item 62, wherein the antibody or antigen-binding fragment thereof is an antibody or antigen-binding fragment thereof against activin receptor type 2B.
66. The method of item 62, wherein the antibody or antigen-binding fragment thereof is an antibody or antigen-binding fragment thereof against activin A.
67. The method according to any one of items 58-66, wherein the rodent is a mouse or a rat.

What is claimed is:

1. A nucleic acid, comprising a modified rodent Activin A receptor type 1 (ACVR1) gene, wherein the modified rodent ACVR1 gene comprises
   a) an ACVR1 exon 7 in sense orientation flanked by a first pair of site-specific recombinase recognition sites (SRRSs), wherein the ACVR1 exon 7 encodes the same amino acid sequence as a wild-type exon 7 of a human ACVR1 gene; and
   b) a mutant exon 7 of a rodent ACVR1 gene in antisense orientation encoding a R258G substitution flanked by a second pair of SRRSs that are different from the first pair of SRRSs;
   wherein the exon 7 in sense orientation:
   i) is the wild-type exon 7 of the human ACVR1 gene; or
   ii) has decreased sequence identity to the mutant exon 7 of the rodent ACVR1 gene as compared to the wild-type exon 7 of the human ACVR1 gene; and
   wherein the first and second pairs of SRRSs are oriented so that a recombinase can invert the mutant exon 7 into sense orientation and delete the exon 7 in sense orientation to form a mutant ACVR1 gene comprising the mutant exon 7.

2. The nucleic acid of claim 1, wherein the exon 7 in sense orientation has decreased sequence identity to the mutant exon 7 of the rodent ACVR1 gene as compared to the wild-type exon 7 of the human ACVR1 gene.

3. The nucleic acid of claim 1, wherein the activity of the recombinase is inducible.

4. The nucleic acid of claim 1, wherein the recombinase is Cre.

5. The nucleic acid of claim 1, wherein the rodent is a mouse.

6. A construct for targeted modification of an ACVR1 gene in a rodent genome, comprising a nucleic acid sequence which comprises:
   a) an ACVR1 exon 7 in sense orientation flanked by a first pair of site-specific recombinase recognition sites (SRRSs), wherein the ACVR1 exon 7 encodes the same amino acid sequence as a wild-type exon 7 of a human ACVR1 gene; and
   b) a mutant exon 7 of a rodent ACVR1 gene in antisense orientation encoding a R258G substitution flanked by a second pair of SRRSs that are different from the first pair of SRRSs;
   wherein the exon 7 in sense orientation:
   i) is the wild-type exon 7 of the human ACVR1 gene; or
   ii) has decreased sequence identity to the mutant exon 7 of the rodent ACVR1 gene as compared to the wild-type exon 7 of the human ACVR1 gene; and
   wherein the first and second pairs of SRRSs are oriented so that a recombinase can invert the mutant exon 7 into sense orientation and delete the exon 7 in sense orientation to form a mutant ACVR1 gene comprising the mutant exon 7; and
   wherein said nucleic acid sequence is flanked by homology arms capable of mediating integration of said nucleic acid sequence into the rodent ACVR1 gene.

7. The construct of claim 6, wherein the exon 7 in sense orientation has decreased sequence identity to the mutant exon 7 of the rodent ACVR1 gene as compared to the wild-type exon 7 of the human ACVR1 gene.

8. The construct of claim 6, wherein the first and second pairs of SRRS are Lox2372 and LoxP or vice versa.

9. The construct of claim 6, wherein the recombinase is Cre.

10. The construct claim 6, wherein the rodent is a mouse.

11. The of claim 1, wherein the rodent is a rat.

12. The construct of claim 6, wherein the rodent is a rat.

* * * * *

```
SEQUENCE LISTING

Sequence total quantity: 8
SEQ ID NO: 1               moltype = DNA  length = 147
FEATURE                    Location/Qualifiers
source                     1..147
                           mol_type = genomic DNA
                           organism = Homo sapiens
SEQUENCE: 1
ggaaaggcag gtatggtgag gtgtggaggg gcagctggca aggggagaat gttgccgtga  60
agatcttctc ctcccgtgat gagaagtcat ggttcaggga aacggaattg tacaacactg 120
tgatgctgag gcatgaaaat atcttag                                     147

SEQ ID NO: 2               moltype = DNA  length = 147
FEATURE                    Location/Qualifiers
misc_feature               1..147
                           note = Synthetic Polynucleotide
source                     1..147
                           mol_type = other DNA
                           organism = synthetic construct
SEQUENCE: 2
ggaagggag atacggtgag gtgtggcgcg gatcttggca gggagagaac gttgccgtca  60
aaatttttag cagccgtgat gaaaaaagct ggtttagaga aacagagctc tataatacag 120
tcatgctgag gcacgagaac attctgg                                     147

SEQ ID NO: 3               moltype = DNA  length = 374
FEATURE                    Location/Qualifiers
misc_feature               1..374
                           note = Synthetic Polynucleotide
source                     1..374
                           mol_type = other DNA
                           organism = synthetic construct
SEQUENCE: 3
agcaatggag ggattaagag ttgcatgcac taaattaatt attcttaatg atgggctggc  60
tgcctccaaa atgactactg ttctgtgtca cctatgtttt gcttttcata gggaaaggga 120
gatacggtga ggtgtggcgc ggatcttggc agggagagaa cgttgccgtc aaaatttta 180
gcagccgtga tgaaaaaagc tggtttagag aaacagagct ctataataca gtcatgctga 240
ggcacgagaa cattctgggt aagtacaagg ataaccccct cattaattgt atctagggag 300
aaacaattgt ctgcctttgc tctctccgtt ttggtgaatg tgaattcgag agtgtctcct 360
aaaaagcaat atag                                                   374

SEQ ID NO: 4               moltype = DNA  length = 147
FEATURE                    Location/Qualifiers
source                     1..147
                           mol_type = genomic DNA
                           organism = Mus musculus
SEQUENCE: 4
ggaagggccg gtatggagaa gtatggaggg gcagctggca aggcgaaaat gtcgctgtga  60
agatcttctc ctcccgagac gagaagtcat ggttcaggga gacggaattg tacaacactg 120
tgatgttggg gcatgaaaat atcttag                                     147

SEQ ID NO: 5               moltype = DNA  length = 147
FEATURE                    Location/Qualifiers
source                     1..147
                           mol_type = genomic DNA
                           organism = Mus musculus
SEQUENCE: 5
ctaagatatt ttcatgcccc aacatcacag tgttgtacaa ttccgtctcc ctgaaccatg  60
acttctcgtc tcgggaggag aagatcttca cagcgacatt ttcgccttgc cagctgcccc 120
tccatacttc tccataccgg cccttcc                                     147

SEQ ID NO: 6               moltype = DNA  length = 372
FEATURE                    Location/Qualifiers
source                     1..372
```

```
                        mol_type = genomic DNA
                        organism = Mus musculus
SEQUENCE: 6
gagaagagca ggaggttcaa atataaggac actgtcgggt tcactgtgtt tgagaggaaa    60
aggaaagcca acccatttct tacatatatc atctgttttg ctgtccacag ggaagggccg   120
gtatggagaa gtatggaggg gcagctggca aggcgaaaat gtcgctgtga agatcttctc   180
ctcccgagac gagaagtcat ggttcaggga gacggaattg tacaacactg tgatgttggg   240
gcatgaaaat atcttaggtg agtaccaggt gagctttcac cagctggtct ccatagagat   300
aagggccggc cctttctctc tcccatttgc caaatctgag gtgtgtggag tctcttctgg   360
aaaacaacat ag                                                       372

SEQ ID NO: 7            moltype = DNA  length = 372
FEATURE                 Location/Qualifiers
source                  1..372
                        mol_type = genomic DNA
                        organism = Mus musculus
SEQUENCE: 7
ctatgttgtt ttccagaaga gactccacac acctcagatt tggcaaatgg gagagagaaa    60
gggccggccc ttatctctat ggagaccagc tggtgaaagc tcacctggta ctcacctaag   120
atattttcat gccccaacat cacagtgttg tacaattccg tctccctgaa ccatgacttc   180
tcgtctcggg aggagaagat cttcacagcg acattttcgc cttgccagct gcccctccat   240
acttctccat accggcectt ccctgtggac agcaaaacag atgatatatg taagaaatgg   300
gttggctttc cttttcctct caaacacagt gaacccgaca gtgtccttat atttgaacct   360
cctgctcttc tc                                                       372

SEQ ID NO: 8            moltype = DNA  length = 147
FEATURE                 Location/Qualifiers
source                  1..147
                        mol_type = genomic DNA
                        organism = Rattus norvegicus
SEQUENCE: 8
ggaagggccg gtatggagaa gtgtggaggg gcagctggca aggcgaaaat gttgctgtga    60
agatcttctc ctcccgtgat gagaagtcgt ggttcaggga gacagaattg tacaacacgg   120
tgatgctgag gcatgagaat atcttag                                       147
```